United States Patent [19]

Sato

[11] 4,040,412
[45] Aug. 9, 1977

[54] BIOELECTRODES

[76] Inventor: Takuya R. Sato, 5130 Randall St., Culver City, Calif. 90230

[21] Appl. No.: 655,030

[22] Filed: Feb. 3, 1976

Related U.S. Application Data

[63] Continuation-in-part of Ser. No. 495,957, Aug. 9, 1974, abandoned, which is a continuation-in-part of Ser. No. 228,827, Feb. 24, 1972, Pat. No. 3,834,373.

[51] Int. Cl.² .............................................. A61B 5/04
[52] U.S. Cl. ............................ 128/2.06 E; 128/2.1 E; 128/417; 128/DIG. 4
[58] Field of Search ............... 128/2.06 E, 2.1 E, 404, 128/410, 411, 417, 418, DIG. 4

[56] References Cited

U.S. PATENT DOCUMENTS

| 2,651,304 | 9/1953 | Browner | 128/417 |
|---|---|---|---|
| 3,170,459 | 2/1965 | Phipps et al. | 128/2.06 E |
| 3,187,745 | 6/1965 | Baum et al. | 128/2.06 E |
| 3,545,432 | 12/1970 | Berman | 128/2.06 E |
| 3,659,614 | 5/1972 | Jankelson | 128/410 |
| 3,669,110 | 6/1972 | Low | 128/2.1 E |
| 3,669,119 | 6/1972 | Symmes | 128/410 |
| 3,828,766 | 8/1974 | Krasnow | 128/2.1 E |
| 3,830,229 | 8/1974 | Johnson | 128/2.06 E |
| 3,845,757 | 11/1974 | Weyer | 128/2.1 E |

FOREIGN PATENT DOCUMENTS

| 1,163,803 | 5/1958 | France | 128/418 |
|---|---|---|---|

Primary Examiner—Robert W. Michell
Assistant Examiner—Lee S. Cohen

[57] ABSTRACT

A bioelectrode applicable to a body part has a pouch having a solid bottom formed of a sheet of electrically insulating watertight material being solid throughout said bottom, and a top sealed to said bottom and having an aperture remote from that bottom. The pouch defines an enclosed interior wider than that aperture. An electrode is located in the pouch and is spaced from the mentioned aperture. An electrolyte-absorbing pad is located in the pouch between the electrode and the mentioned aperture and extends in the above mentioned closed interior beyond the width of the aperture.

Another bioelectrode applicable to a body party has a pouch having a bottom formed of a sheet of electrically insulating watertight material having a hole, and a top sealed to the bottom and having an aperture remote from the bottom. The pouch defines an enclosed interior wider than the latter aperture. An electrode in the pouch is spaced from the mentioned aperture. The hole in the bottom is closed by a watertight seal formed with the aid of a device providing an electric current conducting lead from the electrode to the outside of the pouch. An electrolyte-absorbing pad extends in the above mentioned enclosed interior beyond the width of the aperture, being in contact with the electrode and accessible at the aperture.

72 Claims, 13 Drawing Figures

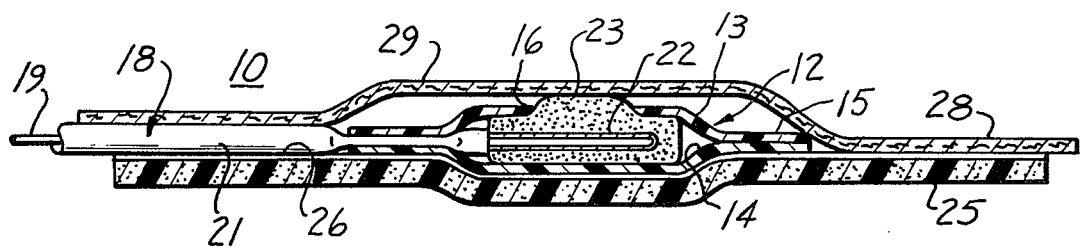
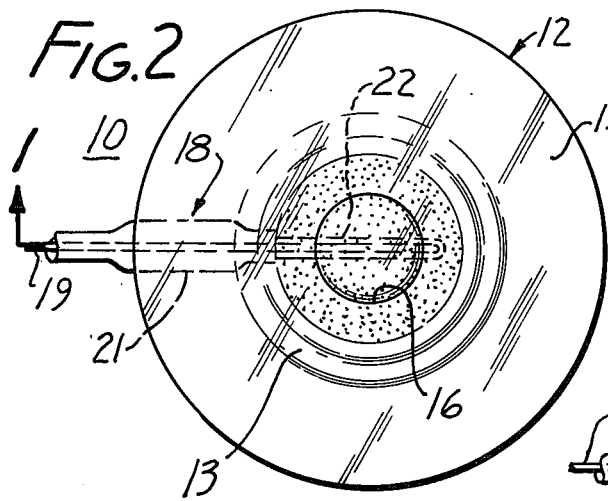
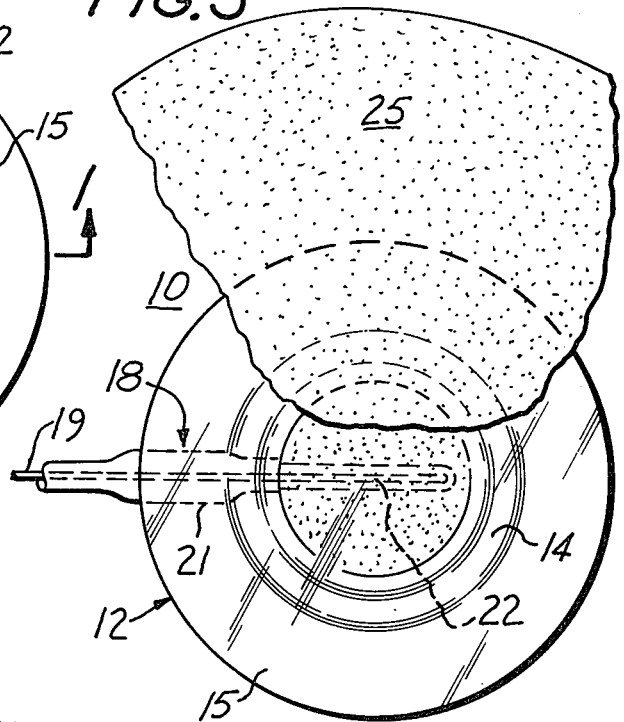
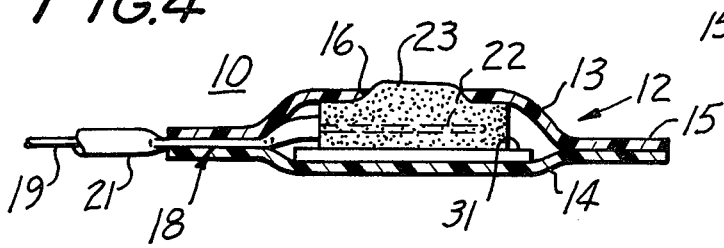
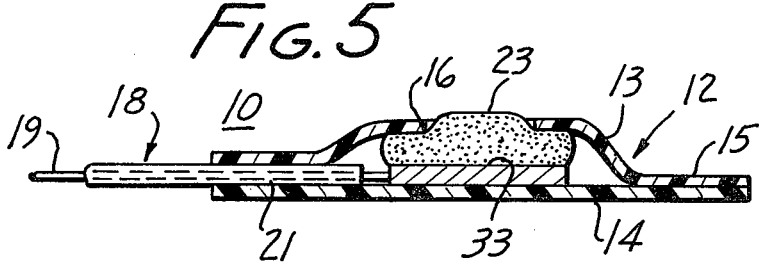

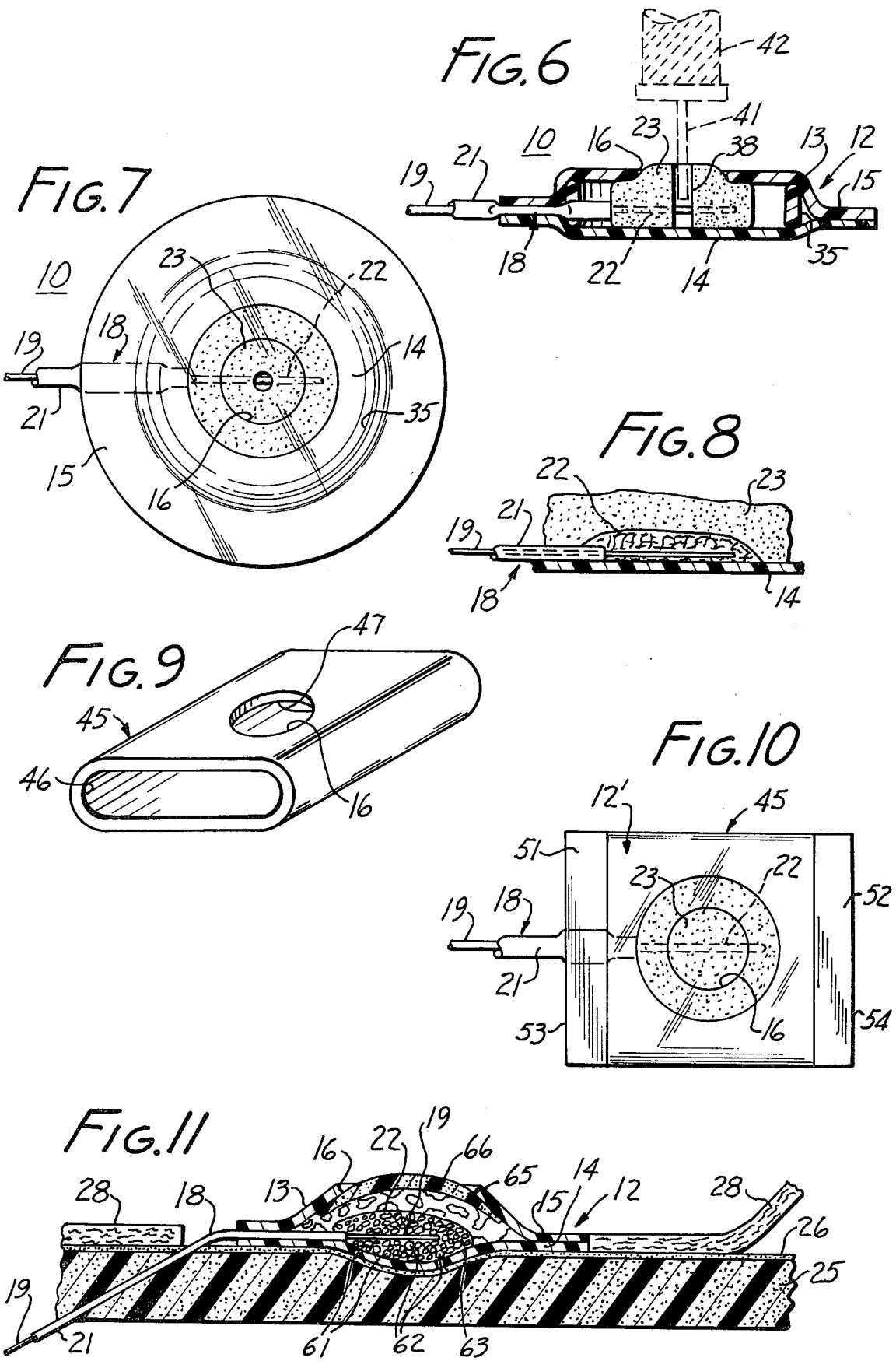

BIOELECTRODES

CROSS-REFERENCE

This is a continuation-in-part of the allowed United States patent application Ser. No. 495,957, entitled Bioelectrodes, and filed on Aug. 9, 1974, now abandoned, as a continuation-in-part of the United States Patent application Ser. No. 228,827, entitled Silver, Silver Chloride Electrodes, filed on Feb. 24, 1972, and issued on Sept. 10, 1974 as U.S. Pat. No. 3,834,373.

BACKGROUND OF THE INVENTION

1. Field of the Invention

The subject invention relates to bioelectrodes applicable to body parts of living subjects to detect electrical signals and for similar purposes.

2. Description of the Prior Art

Despite a wealth of existing bioelectrodes and prior-art proposals for their improvements, there persists a need for a type of bioelectrode that is more suitable to mass production with modern techniques and equipment and that is less expensive to its end user while maintaining the performance characteristics of high-quality prior-art electrodes. Some prior-art proposals which have tended in that direction, such as those propounded in the U.S. Pat. Nos. 3,464,404 and 3,518,984, by R. E. Mason, issued Sept. 2, 1969 and July 7, 1970, respectively, were, nevertheless, unsuitable because of such factors as dissipation of electrolyte through the back of the bioelectrode and generation of artifactitious signals and extrusion of electrolyte, with concomitant contamination of the adhesive or attachment surface, through lack of physical stability. More recent prior-art endeavors thus again tended in the direction of the more expensive and complex cup-type electrode design. This despite the availability of pouch designs in other areas, such as seen in U.S. Pat. No. 3,556,105, by L. B. Shepard, issued Jan. 19, 1971, and U.S. Pat. No. 3,669,119, by P. S. Symmes, issued June 13, 1972, and of bioelectrode design features as for, instance, apparent from U.S. Pat. Nos. 3,170,459; 3,187,745; 3,545,432; 3,610,229; 3,606,881; 3,659,614 and 3,669,110, and from French Pat. No. 1,163,803, by Electromedica.

SUMMARY OF THE INVENTION

It is a broad object of the invention to satisfy the above mentioned need.

It is a related object of the invention to provide improved bioelectrodes.

It is a more specific object of the invention to provide pouch-type bioelectrodes in which the electrolyte is preserved against evaporation and dissipation.

It is also an object of the invention or provide pouch-type bioelectrodes in which electrolyte may be stored by the manufacturer, and to provide improved methods for charging bioelectrodes with electrolyte.

It is also an object of the invention to provide bioelectrodes characterized by an improved retention of the electrode on the applied body part.

It is a related object of the invention to provide pouch-type bioelectrodes with rigidifying means for increased physical stability and decreased artifactitious signal generation.

Other objects of the invention will become apparent in the further course of this disclosure.

From one aspect thereof, the invention resides in a bioelectrode applicable to a body part, comprising in combination a pouch having a solid bottom formed of a sheet of electrically insulating watertight material being solid throughout said bottom, and a top sealed to said bottom and having an aperture remote from said bottom, said pouch defining an enclosed interior wider than said aperture, electric current conducting means including an electrode in said pouch spaced from said aperture and means for connecting said electrode to external electronic equipment, and electrolyte-absorbing means in said pouch in contact with said electrode and exposed at said aperture, said electrolyte absorbing means extending in said enclosed interior beyond the width of said aperture.

From another aspect thereof, the invention resides in a bioelectrode applicable to a body part, comprising in combination a pouch formed of electrically insulating material and having an aperture and a solid bottom remote from said aperture, and defining an enclosed interior wider than said aperture, electric current conducting means including an electrode in said pouch spaced from said aperture and means for connecting said electrode to external electronic equipment, electrolyte-absorbing means in said pouch in contact with said electrode and exposed at said aperture, said electrolyte-absorbing means extending in said enclosed interior beyond the width of said aperture, and an adhesive sheet for retaining said pouch on said body part, said pouch being located on said adhesive sheet, with said bottom being closer to said adhesive sheet than said aperture, and with said adhesive sheet having an adhesive portion surrounding said pouch.

From a further aspect thereof, the invention resides in a bioelectrode applicable to a body part, comprising in combination a pouch formed of electrically insulating material and having an aperture and a solid bottom remote from said aperture, and defining an enclosed interior vider than said aperture, electric current conducting means including an electrode in said pouch spaced from said aperture and means for connecting said electrode to external electronic equipment, electrolyte absorbing means in said pouch in contact with said electrode and exposed at said aperture, said electrolyte-absorbing means extending in said enclosed interior beyond the width of said aperture, and means in said pouch for rigidifying said pouch.

From a further aspect thereof, the invention resides in a bioelectrode applicable to a body part, comprising in combination a sheet of electrically insulating watertight material forming a pouch defining a closed interior and having a bottom formed by a portion of said sheet being solid throughout said bottom, and a top formed by a further portion of said sheet having an aperture remote from said bottom and being attached to said solid bottom-forming portion by a watertight seal integral with said solid bottom-forming portion and said further portion, electric current conducting means including an electrode in said pouch spaced from said aperture and means for connecting said electrode to external electronic equipment, and electrolyte-absorbing means in said pouch in contact with said electrode and exposed at said aperture.

BRIEF DESCRIPTION OF THE DRAWINGS

The subject invention and its objects will become more readily apparent from the following detailed description of preferred embodiments thereof, illustrated by way of example in the accompanying drawings in which like reference numerals designate like or functionally equivalent parts and in which:

FIG. 1 is a section through a bioelectrode according to a preferred embodiment of the subject invention, taken along the line 1 — 1 in FIG. 2;

FIG. 2 is a top view of the bioelectrode of FIG. 1, with certain parts having been removed for better visibility of the electrode structure;

FIG. 3 is a bottom view of the bioelectrode of FIG. 1, with a certain part having been partially broken away for beter visibility of the electrode structure;

FIG. 4 is a view similar to FIG. 1 illustrating a modification of the bioelectrode of FIG. 1 in accordance with a preferred embodiment of the subject invention;

FIG. 5 is a view similar to FIG. 1 illustrating a modification of the bioelectrode of FIG. 1 in accordance with yet another preferred embodiment of the subject invention;

FIG. 6 is a view similar to FIG. 1, illustrating a modification of the bioelectrode of FIG. 1 in accordance with a further preferred embodiment of the subject invention;

FIG. 7 is a top view of the bioelectrode of FIG. 6;

FIG. 8 is a detail view illustrating a modification that may be employed in the bioelectrodes of the subject invention;

FIG. 9 is a perspective view of an enclosure that may be employed in the manufacture of bioelectrodes in accordance with a preferred embodiment of the subject invention;

FIG. 10 is a top view of a bioelectrode utilizing the enclosure of FIG. 9 and embodying the subject invention;

FIG. 11 is a view similar to FIG. 1 showing a bioelectrode in accordance with yet another preferred embodiment of the subject invention;

DESCRIPTION OF PREFERRED EMBODIMENTS

Figure 12:
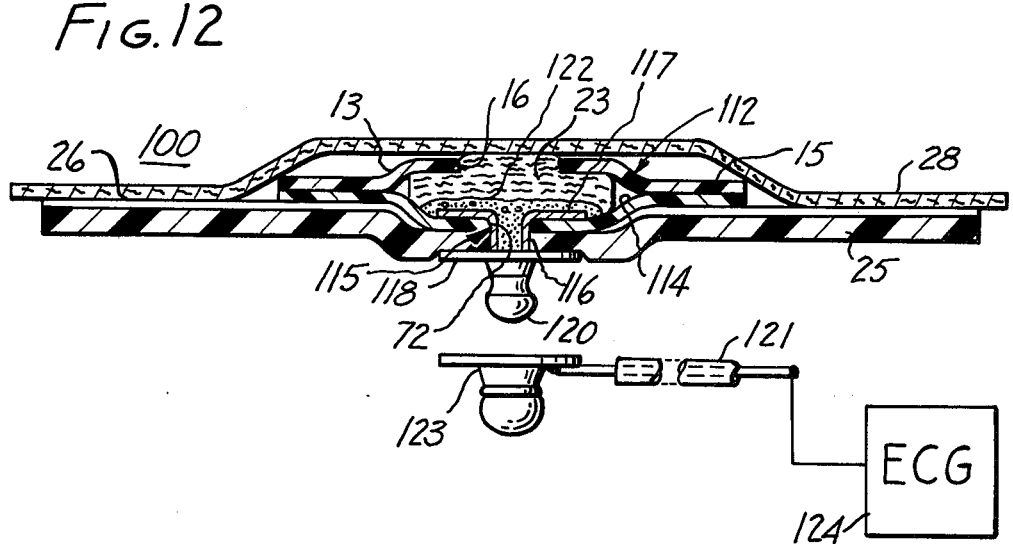
FIG. 12 is a view similar to FIG. 1 showing a bioelectrode in accordance with yet another preferred embodiment of the subject invention.

The utility of the bioelectrodes according to the subject invention in general, and the bioelectrodes shown in the illustrated preferred embodiments in particular, extends from fields involving the measurements of electrical body signals to other areas, such as those concerned with the application of electric currents or the iontophoretic application of substances to body parts.

The bioelectrode 10 shown in FIGS. 1 to 3 comprises a pouch 12 composed of sheets 13 and 14 interconnected by a watertight seal 15. The sheet 13 has an aperture 16 and the seal 15 is spaced from that aperture.

An electric current conducting means 18 includes a lead wire 19 provided with an electrical insulation 21 and an active electrode 22. The electric lead 19 extends from the outside of the pouch 12 through the seal 15 into the pouch and serves to connect the bioelectrode 10 to suitable electronic equipment (not shown), as disclosed in the above mentioned parent application or patent and as generally known in the bioelectrode art.

The electrode 22 may comprise the type of silver, silver chloride electrode disclosed and covered in the above mentioned parent application or patent which is herewith incorporated by reference herein. Briefly, that type of silver, silver chloride electrode comprises a plurality of silver particles, a plurality of silver chloride particles, and an electrically insulating, water impermeable, inert organic matrix for said silver particles and said silver chloride particles, with the silver particles and the silver chloride particles being interspersed with each other in and throughout the matrix, and these interspersed silver particles and silver chloride particles being in electrical contact with each other. For present purposes, the silver particles, or the silver particles and the silver chloride particles, or particles of equivalent function, may be referred to as "particles of electrode material". In that case, the electrode 22 may be said to comprise particles of electrode material and a matrix for the electrode material particles, such as the above mentioned electrically insulating, water impermeable, inert organic matrix. It should, however, be understood that the practice of the subject invention and its utility is not limited to any particular electrode material or type of electrode.

As, for instance, shown in FIG. 1, the electrode 22 is spaced from the pouch aperture 16. This is essential to avoid direct contact of the electrode 22 with body parts to which the bioelectrode of the subject invention is applied. Such direct contact would prevent proper operation of the electrode in its requisite electrolytic environment and would also introduce artifactitious signals or motion generated noise into the detected electrical body signals, thereby rendering the bioelectrode inoperative for its intended purpose.

In accordance with an important feature of one of the inventions herein disclosed, the pouch 12 has a solid bottom formed by the sheet 14 which is solid throughout said bottom. This distinguishes the illustrated preferred embodiment from prior-art proposals where the bottom of the bioelectrode had an aperture for passage of the electrode lead wire. That construction encumbered the manufacturing process and provided an undesirable escape path for electrolyte.

Further according to the subject invention, an electrolyte-absorbing means, such as an electrolyte-absorbing pad 23, is located in the pouch 12. At least a portion of the electrolyte-absorbing means has to be located between the electrode 22 and the pouch aperture 16.

According to the preferred embodiment shown in FIGS. 1 to 3, the electrode 22 extends into the electrolyte pad 23. In particular, the electrode 22 covers an end of the wire 19 and it is that covered end portion which is pierced into the pad 23. By way of example, the conductor 19 may be covered by the above mentioned matrix of the electrode 22 and may be in electric contact with the silver and silver chloride particles or with other electrode material particles of the electrode 22.

Installation of the electrode 22 in the pad 23 has the substantial advantage of establishing a firm physical and motion insensitive contact between the electrode 22 and the electrolyte in the pad 23.

In the illustrated preferred embodiment shown in FIGS. 1 to 3, the pouch seal 15 extends about the electrolyte-absorbing means or pad 23 and is of circular configuration. In practice, this is a very advantageous construction from the point of view of ease of mass production, of easy applicability of the bioelectrode to body parts, and of high motion insensitivity of the electrode.

According to the illustrated preferred embodiment of the invention, the pouch 12 defines an enclosed interior wider than the aperture 16. The electrolyte-absorbing means or pad 23 extends in the enclosed interior in the pouch 12 beyond the width of the aperture 16, and is in contact with the electrode 22 and accessible or exposed at the aperture 16.

According to the illustrated preferred embodiment of the invention, the only aperture in the sheets forming the pouch 12 is the aperture 16 in the sheet 13 forming the top of the bioelectrode pouch. This aperture is remote from the solid pouch bottom. The lead 19 with insulation 21 extends in between the sheets 13 and 14, rather than through either of them. This most fully preserves the watertight quality of the bottom sheet 14 and of the top sheet 13 adjacent the pouch aperture 16.

The pad 23 is exposed at the pouch aperture 16 for intimate contact of itself and of the electrolyte it carries with the body part to which the bioelectrode 10 is applied. Further in accordance with the preferred embodiment shown in FIGS. 1 to 10, it will be noted that the electrolyte pad 23 is also in physical contact with the electrode 22.

In practice of the subject invention, the use of pore and cell-free materials for the sheets 13 and 14 for providing a watertight pouch 12 is preferred. Suitable materials include polyvinyl chloride, polyethylene, an unsaturated polyester resin, and sheets of an ionomer resin. The sheets 13 and 14 are preferably heat sealed to each other and to the electrical insulation 21 to provide a watertight seal 15. To this end, the electrical insulation 21 of the lead 19 is preferably made of thermoplastic material.

To make the bioelectrode easily attachable to, and to improve the retention of the bioelectrode on, parts of the body, a pad or sheet 25 of a soft material, such as rubber, closed-cell polyurethane foam, or closed-cell polyethylene foam is provided with an adhesive coating 26. The adhesive 26 may be a commercially available, medical-grade pressure sensitive adhesive.

The pouch electrodes herein shown are located in the adhesive sheet 25, with the bottom sheet 14 being closer to the adhesive sheet 25 than the pouch aperture 16 which is remote from the sheet 25, and with the adhesive sheet 25 having an adhesive portion surrounding the pouch 12. It is to be understood that all pouch electrodes herein disclosed may be located on an adhesive sheet of the type or kind shown at 25 in FIGS. 1, 3, 11 and 12.

In accordance with an important feature of one of the inventions herein disclosed, the adhesive sheet 25 or equivalent means serve in combination with the pouch electrode to eliminate artifactitious signals and other disturbances by retaining the pouch electrode securely on the applied body part, thereby imparting to the pouch electrode a beneficial rigidity against undesired motion effects which would introduce artifacts into the electrode signal. By means of this combination of pouch electrode and adhesive sheet, the structural, manufacturing and price advantages of pouch-type electrodes may be taken advantage of without exposure to the detriments associated with that type of bioelectrode.

This constitutes a very significant improvement over prior-art electrodes in which the adhesive was on the top sheet adjacent the electrolyte aperture and was thus of no benefit to electrode rigidity and desired immobility.

In the illustrated preferred embodiment, the pouch 12 is located on a central portion of the adhesive sheet 25, with the aperture 16 being remote and facing away from the adhesive sheet 25 and the bottom sheet 14 being attached and securely held on the adhesive sheet 25 by the adhesive 26.

A peelable glazed protective strip 28 has a peripheral portion located on the adhesive 26 and has a central portion shaped in the manner of a cap 29 for protecting the bioelectrode during shipment and storage.

The strip 28 may have the same circular configuration as the adhesive sheet 25 and is, of course, peeled from the sheet prior to the application of the bioelectrode to a body part.

In principle, it is within the scope of the subject invention that the electrolyte pad 23 be of a foamed synthetic material that is not necessarily hydrophilic of itself, but that has a sufficient number of internal open cells for the absorption of electrolyte by the pad 23. For instance, the pad 23 may be of foamed open-cell urethane. However, to render the bioelectrode less sensitive to compression and to compression followed by expansion, and to avoid an interruption of the electrolytic paths in the pad 23, I much prefer the use of a hydrophilic material for the electrolyte pad.

In this respect, several natural or man-made structures are suitable for the electrolyte pad as long as they possess fibers, membranes or wall portions capable of hydrophilically taking up the aqueous or liquid electrolyte employed in the bioelectrode 10. Suitable specific examples include felt, blotting paper, a natural sponge, and a man-made cellulose sponge.

According to the preferred embodiment shown in FIGS. 4 to 7, the bioelectrode 10 includes and the pouch 12 contains means for rigidifying the pouch to further reduce the electrode's motion insensitivity.

In particular, the bioelectrode 10 according to FIG. 4 includes a reinforcing member in the form of a disk 31 located on the sheet 14 adjacent a portion of the pouch 12 opposite the pouch aperture 16. In the illustrated preferred embodiment, the disk 31 supports the electrolyte pad 23 and the electrode 22 contained therein. The disk 31, like the sheets 13 and 14, may be of electrically insulating material to avoid interference with the proper operation of the bioelectrode. By way of example, the disk 31 may be of one of the synthetic materials mentioned above for the sheets 13 and 14. In practice, the disk 31 is preferably thicker than the sheets 13 and 14, but may be of a different material.

In the preferred embodiment shown in FIG. 5, the pouch reinforcing means are provided by the electrode itself. In particular, the wire-type electrode 22 shown in FIGS. 1 to 4 is in FIG. 5 replaced by a disk-type electrode 33 to which the wire 19 is electrically connected. For instance, the electrode 33 may comprise a silver disk which is preferably provided with a surface layer of silver chloride (not shown) in a conventional manner, to improve the performance of the bioelectrode in accordance with well-known electrochemical principles.

In the preferred embodiment shown in FIGS. 6 and 7, the pouch rigidifying means comprise an annulus 35 which may be of the same material as the disk 31, and which encompasses at least the electrolyte-absorbing means or pad 23.

In the preferred embodiment shown in FIGS. 6 and 7, the annulus 35 also encompasses the electrode 22. By way of further example, a suitable material for the annulus 35, and also for the disk 31, is nylon.

As seen in FIG. 6, the electrolyte pad 23 is preferably spaced circularly from the annulus 35 to render the electrolyte paths in the pad 23 less vulnerable to rupture upon compression and subsequent relaxation of the pad.

FIGS. 6 and 7 also illustrate a method according to the subject invention for supplying electrolyte to the electrolyte-absorbent means or pad 23. In particular, the electrolyte pad 23 is provided with a bore 38. The word "bore" as herein employed is not intended to designate or limit the manner in which the hole or bore 38 is made. Indeed, the bore 38 may be made by punching the pad 23 with a suitable tool or the bore 38 may otherwise be provided during the manufacture of the pad and in a permanent manner.

Further in accordance with the subject invention, part of a hollow needle shown in dotted outline in FIG. 6 is inserted into the bore 38 and the desired electrolyte is forced through the inserted needle 41 into the pad 23. A syringe or other pressurized electrolyte supply device is shown in dotted outline at 42 for forcing electrolyte into the inserted needle 41.

In practice, the method illustrated in FIG. 6 has proved to increase the speed of mass production and the uniformity of electrolyte application very considerably. In the dry state, the pad 23 is typically thinner than in its electrolyte-saturated state. When the dry pad 23 is supplied with the desired electrolyte, it will typically swell, moving the sheets 13 and 14 away from each other until relative further travel thereof is limited by the integral seal 15. At that juncture, the electrolyte saturated pad 23 commences to bulge out of the pouch aperture 16 for an intimate contact with the applied body part for maximum efficiency and performance quality of the bioelectrode.

In accordance with the further preferred embodiment shown in FIG. 8, the electrode 22 is located on the sheet 14 of electrically insulating material. In particular, the electrode 22 may have an organic matrix of the above mentioned type which bonds the electrode 22 to the sheet 14 and thereby to the inside of the pouch 12 or to its solid bottom.

It is a feature of the subject invention that the electrode pouch comprises at least one sheet of electrically insulating material. In the preferred embodiment shown in FIGS. 8 and 9, only one sheet 45 of electrically insulating material is employed for making the pouch. By way of example, the sheet 45 may be made of one of the heat-sealable materials mentioned above for the sheets 13 and 14.

In particular, the one sheet of electrically insulating watertight material which forms the solid pouch bottom also forms the pouch top containing the pouch aperture 16. Of course, the portion of the sheet which forms the bottom is solid throughout such bottom, while the top-forming portion of the sheet has the mentioned aperture 16 remote from the bottom and is sealed to the bottom-forming portion of that sheet.

As best seen in FIG. 9, the sheet 45 is endless in the sense of being closed in itself. The pouch aperture 16 may be provided in the endless sheet 45 as seen in FIG. 9, and the space enclosed by the endless sheet 45 has two terminal openings 46 and 47.

The electrolyte pad 23 and the electrode 22 may be assembled outside of the pouch by piercing the electrode into the pad. The assembled electrode and pad are then inserted into the space within the endless sheet 45 through either of the openings 46 and 47. The electrode 22 and pad 23 are thereby located adjacent the pouch aperture 16 as shown.

In the preferred embodiment shown in FIG. 10, two parallel seals 51 and 52 are integral with the endless sheet 45 and perform the function of the above mentioned circular seal 15 in the other embodiments. In particular, the integral seal 51 interconnects adjacent portions of the endless sheet 45 along a first margin 53 thereof in order to seal the opening 46. Similarly, the integral watertight seal 52 interconnects adjacent portions of the endless sheet 45 along a second margin 54 thereof spaced from the first margin 53, in order to close the other opening 47.

The sheet 45 may also be thought as folded upon itself and the seals 51 and 52 as interconnecting adjacent edge portions of such folded sheet.

The embodiment of FIGS. 9 and 10 is highly advantageous in terms of ease of manufacture, structural integrity, and high quality of performance.

The one sheet 45 need not be necessarily endless, but may merely be folded upon itself to form the requisite top and bottom portions of the pouch. Adjacent edge portions of that folded sheet are then sealed to each other to provide the requisite pouch.

A disposable bioelectrode in accordance with a further preferred embodiment of the invention is shown in FIG. 11.

According to FIG. 11, the insulated electrical wire 19 has a non-insulated end portion inside the pouch 12. The wire may be of silver or at least the end portion inside the pouch may be silver plated. The electrically conductive wire end portion is embedded in a silver, silver chloride electrode 22 of the above mentioned type. As mentioned above, the electrode 22 may have silver particles shown at 61 and silver chloride particles shown at 62 interspersed in an organic matrix 63.

The electrode 22 of FIG. 11 has an open-cell rigid member 65 located thereon. The member 65 may be of open-cell urethane or other open-cell rigid plastic. Another suitable material for the member 65 is foam glass. The rigid open-cell member retains electrolyte without undue mobility thereof. A flexible pad or sponge 66, which may be of the same material as the pad 23 in the other embodiments, is located on top of the rigid member 65 and is exposed at the pouch aperture 16 for contact with the applied body part. In practice, electrolyte is applied to the sponge 66 until the pores of the rigid member 65 have been filled. In this manner, the flexible sponge 66, which serves as a shock absorber isolating the electrode 22 from mechanical disturbances emanating from body parts, and as a retainer of electrolyte, is spaced from the electrode 22 and the open-cell rigid member 65 is located between the flexible sponge or pad and the electrode 22.

The electrode 22, member 65 and sponge 66 are packaged in a laminate which is composed of the heat-sealed plastics sheets 13 and 14 forming the pouch 12.

In accordance with a preferred manufacture of the bioelectrode device of FIG. 11, the silver chloride-doped resin and catalyst mixture is applied to the free end portion of the wire 19 in an uncured state. The uncured electrode mass with the embedded wire portion is then placed onto the lower sheet 14 of the laminate. The rigid porous member 65 is then placed on top of the uncured electrode mass. The sponge member 66 is placed on top of the rigid porous member 65, and the top sheet 13 is placed on top of the whole assembly so that the central portion of the sponge 66 is exposed at the aperture 16. The laminate may then be heat sealed to provide the integral circular seal 15 and the electrode mass may be cured in one operation, if desired.

The heat-sealed assembly is then attached to the pad 25 by means of the adhesive layer 26. A peelable protective paper layer 28 is provided as before and may have a protective cup of the type indicated at 29 in FIG. 1.

All bioelectrodes herein disclosed may further be sealed in a moisture and airtight package of a metal or plastics foil (not shown).

Various modifications and variations within the spirit and scope of the subject invention will be suggested or rendered obvious to those skilled in the art by the subject extensive disclosure.

Figure 13:
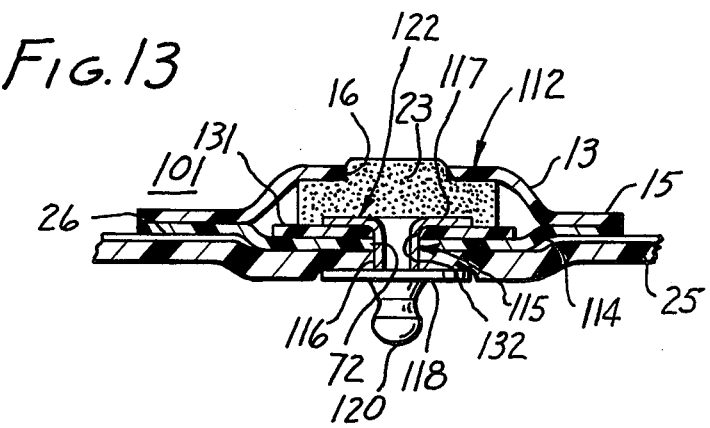
FIG. 13 is a view similar to FIG. 4 showing a bioelectrode in accordance with a further preferred embodiment of the subject invention.

For instance, the further embodiments of the subject invention shown in FIGS. 12 and 13 realize with the aid of a watertight seal in the bottom a chief advantage of the previously discussed embodiments having a solid or imperforate bottom 14.

The bioelectrodes 100 and 101 shown in FIGS. 12 and 13 are very similar in composition and design to the previously described bioelectrodes, and reference may, for instance, be had to FIGS. 1 to 4 and their above description for an explanation of the nature and function of the parts 13, 23, 25, 26 and 28, the seal 15 and the aperture 16.

Even the bottom 114 of the pouch 112 of the electrode 100 shown in FIG. 12 and of the electrode 101 shown in FIG. 13 may be of the same electrically insulating water-tight material as the solid pouch bottom 14 mentioned above, except that the bottom 114 has a single hole 72. In the preferred embodiments shown in FIGS. 12 and 13, the hole 72 is in the center of the pouch electrode bottom sheet 114. The top is sealed to the bottom by the watertight seal 15 and has the aperture 16 remote from the bottom 114. As in the other embodiments, the pouch 112 defines an enclosed interior wider than the top aperture 16.

The electrode 122 in the embodiment of FIG. 12 may have the same composition as the previously described electrode 22 and is also located in the pouch and spaced from the top aperture 16.

The hole 72 in the pouch bottom 114 is closed with a watertight seal 115. This is an important feature of the preferred embodiment illustrated in FIGS. 12 and 13, in that it avoids the electrolyte losses which have impaired, if not destroyed, the utility of the proposals shown in the U.S. Pat. No. 3,464,404, where electrolyte could escape through a rear opening, or U.S. Pat. No. 3,518,984, where electrolyte could still escape along an electric wire through an aperture in a plastic washer which was only reeved over the wire, or U.S. Pat. No. 3,669,119, where electrolyte could escape between a thread in a support and adjustment shaft and a corresponding thread in a base plate.

According to FIGS. 12 and 13, the watertight seal 115 or the means forming same include an electric current conducting device 116 connected to the electrode 122 and extending through the hole 72 to the outside of the pouch. An electrolyte-absorbing pad or sponge 23 extends in the enclosed pouch interior beyond the width of the top aperture 16, being in contact with the electrode 122 and exposed or accessible at the top aperture 16.

Further according to FIGS. 12 and 13, the bioelectrode 100 or 101 includes the above mentioned sheet 25 for releasably retaining the pouch on a body part with the adhesive 26 after the cover 28 has been pealed off or removed. In the embodiments of FIGS. 12 and 13, the adhesive sheet 25 also forms part of the watertight seal 115 preventing escape of the electrolyte.

In particular, the current conducting device 116 has a portion extending through the adhesive sheet 25 and the hole 72 and clamps the adhesive sheet 25 to the pouch bottom 114 at the hole 72, thereby effectively preventing escape of electrolyte.

In particular, the current conducting device 116 in the preferred embodiments of FIGS. 12 and 13 includes a snap fastener, or the male portion of a snap fastener, to be more exact, composed of two interconnected or swaged parts having flanges 117 and 118. The flanges 117 and 118 of the swaged snap fastener parts clamp the bottom-forming sheet 114 around the hole 72. More specifically, the male snap fastener with its flanges 117 and 118 clamps the adhesive sheet 25 into a watertight union with the pouch bottom 114, thereby sealing off the hole 72.

The male snap fastener part has a pintle 120 for the releasable attachment of a lead or wire 121 via a female snap fastener part 123. In this manner, an electrocardiograph or other electric apparatus may be connected to the electrode 122.

The bioelectrode 101 of FIG. 13 includes a disk 131 which is rigid relative to the flexible pouch 112 or bottom 114 and serves to support the electrode 112 and rigidify the pouch. The disk 131 may be of the same composition and construction as the previously described disk 31, except that it has a hole 132 through which the current conducting device 116 extends. In the preferred embodiment shown in FIG. 13, the male snap fastener part with its flanges 117 and 118 clamps the disk 131 to the bottom 114 at the hole 72. The remainder of the bioelectrode may be the same as in the embodiment of FIG. 12.

In the preferred embodiment shown in FIG. 13, the rigidifying disk 131, the electrode 122 thereabove and the portion of the pouch bottom 114 and adhesive sheet 25 and snap fastener 120 therebelow are clamped into a relatively rigid unit which further minimizes the danger of spurious or artifactitious currents. As shown in FIG. 13, the electrode 122 need not in every case have the type of silver, silver chloride-organic matrix coating shown in FIG. 12 and elsewhere. Rather, the snap fastener flange 117 and adjacent metal portions may be of silver or have a silver plating. To provide for compliance with the Nernst equation, a silver, silver chloride coating is preferred on the electrode 122.

In particular, while the type of electrode 122 shown in FIG. 13 may be used in the preferred embodiment shown in FIG. 12, it should be understood that the type of coated electrode 122 shown in FIG. 12 may preferably be used in the bioelectrode 101 of FIG. 13.

I claim:

1. A bioelectrode applicable to a body part, comprising in combination:
   a pouch having a solid bottom formed of a sheet of electrically insulating watertight material being solid throughout said bottom, and a top sealed to said bottom and having an aperture remote from said bottom, said pouch defining an enclosed interior wider than said aperture;
   electric current conducting means including an electrode in said pouch spaced from said aperture and means for connecting said electrode to external electronic equipment; and
   electrolyte-absorbing means in said pouch in contact with said electrode and exposed at said aperture, said electrolyte-absorbing means extending in said enclosed interior beyond the width of said aperture.

2. A bioelectrode as claimed in claim 1, wherein:

said electrolyte-absorbing means include an electrolyte-absorbing pad exposed at said aperture for contact with said body part.

3. A bioelectrode as claimed in claim 2, wherein: said electrode connecting means include an electric lead connected to said electrode and extending in between said bottom formed of said solid sheet and said top to the outside of said pouch.

4. A bioelectrode as claimed in claim 1, wherein: said pouch includes a watertight seal integral with said top and said sheet forming said bottom; and said electrode connecting means include an electric lead connected to said electrode and extending through said watertight seal to the outside of said pouch.

5. A bioelectrode as claimed in claim 1, wherein: said top is formed of a second sheet of electrically insulating watertight material having said aperture remote from said bottom and being sealed by a watertight seal to said first-mentioned sheet of electrically insulating watertight material forming said solid bottom.

6. A bioelectrode as claimed in claim 1, wherein: said sheet of electrically insulating watertight material forming said solid bottom also forms said top, said sheet having a portion forming, and being solid throughout, said bottom, and a top-forming portion having said aperture remote from said bottom and being sealed to said solid bottom-forming portion.

7. A bioelectrode as claimed in claim 6, wherein: said sheet is folded upon itself to form said top and bottom; and adjacent edge portions of said folded sheet are sealed to each other.

8. A bioelectrode as claimed in claim 6, wherein: said sheet is endless and has a solid portion forming said solid bottom and an apertured portion forming said top having said aperture; and adjacent edge portions of said endless sheet are sealed to each other.

9. A bioelectrode as claimed in claim 1, wherein: said electrode is located on said sheet of electrically insulating material at said solid bottom.

10. A bioelectrode as claimed in claim 1, wherein: said electrode is bonded to said sheet of electrically insulating material at said solid bottom.

11. A bioelectrode as claimed in claim 1, wherein: said electrode comprises particles of electrode material and a matrix for said electrode material particles bonded to said sheet of electrically insulating material at said bottom.

12. A bioelectrode as claimed in claim 1, wherein: said electrode comprises particles of electrode material, a matrix for said electrode material particles, and an electric conductor covered by said matrix and in electric contact with said electrode material particles.

13. A bioelectrode as claimed in claim 1, wherein: said electrode in said pouch extends into said electrolyte-absorbing means.

14. A bioelectrode as claimed in claim 1, wherein: said electrolyte-absorbing means include an electrolyte-absorbing pad in physical contact with said electrode.

15. A bioelectrode as claimed in claim 1, wherein: said electrolyte-absorbing means include a flexible electrolyte-absorbing pad spaced from said electrode and exposed at said aperture for contact with said body part, and an open-cell rigid member located between said flexible pad and said electrode for retaining electrolyte.

16. A bioelectrode as claimed in claim 1, wherein: said bioelectrode includes and said pouch contains means for rigidifying said pouch.

17. A bioelectrode as claimed in claim 16, wherein: said rigidifying means include an annulus encompassing at least said electrolyte-absorbing means.

18. A bioelectrode as claimed in claim 16, wherein: said rigidifying means include a reinforcing member adjacent a portion of said pouch opposite said aperture.

19. A bioelectrode as claimed in claim 16, wherein: said rigidifying means include a disk.

20. A bioelectrode as claimed in claim 1, wherein: said electrode in said pouch includes a disk for supporting said electrolyte-absorbing means.

21. A bioelectrode as claimed in claim 1, wherein: said electrolyte-absorbing means include an electrolye absorbing pad having a central bore exposed at said aperture for the reception of electrolyte.

22. A bioelectrode as claimed in claim 1, including: an adhesive sheet for retaining said pouch on said body part, said pouch being located on said adhesive sheet with a portion of said adhesive sheet exposed in the direction of said electrolyte-absorbing means so that said electrolyte-absorbing means contact said body part when said adhesive sheet retains said pouch on said body part.

23. A bioelectrode as claimed in claim 22, wherein: said pouch is oriented on said adhesive sheet so that said aperture is remote from said adhesive sheet.

24. A bioelectrode as claimed in claim 23, wherein: said solid bottom is attached to said adhesive sheet.

25. A bioelectrode as claimed in claim 1, including: a removable cover for said pouch; and means for removably attaching said cover to said pouch to enclose said aperture.

26. A bioelectrode applicable to a body part, comprising in combination:
a pouch formed of electrically insulating material and having an aperture and a solid bottom remote from said aperture, and defining an enclosed interior wider than said aperture;
electric current conducting means including an electrode in said pouch spaced from said aperture and means for connecting said electrode to external electronic equipment;
electrolyte-absorbing means in said pouch in contact with said electrode and exposed at said aperture, said electrolyte-absorbing means extending in said enclosed interior beyond the width of said aperture; and
an adhesive sheet for retaining said pouch on said body part, said pouch being located on said adhesive sheet, with said bottom being closer to said adhesive sheet than said aperture, and with said adhesive sheet having an adhesive portion surrounding said pouch.

27. A bioelectrode as claimed in claim 26, wherein: said bottom of the pouch is attached to said adhesive sheet; and said aperture of the pouch faces away from said adhesive sheet.

28. A bioelectrode as claimed in claim 26, wherein:

said electrolyte-absorbing means include an electrolyte-absorbing pad exposed at said aperture for contact with said body part.

29. A bioelectrode as claimed in claim 26, wherein:
said electrode connecting means include an electric lead connected to said electrode and extending through said pouch to the outside of said pouch.

30. A bioelectrode as claimed in claim 26, wherein:
said pouch includes at least one sheet of electrically insulating watertight material, and a watertight seal interconnecting adjacent portions of said at least one sheet; and
said electrode connecting means include an electric lead connected to said electrode and extending through said watertight seal to the outside of said pouch.

31. A bioelectrode as claimed in claim 26, wherein:
said electrode is located on said bottom of the pouch.

32. A bioelectrode as claimed in claim 26, wherein:
said electrode is bonded to said bottom of the pouch.

33. A bioelectrode as claimed in claim 26, wherein:
said electrode comprises particles of electrode material and a matrix for said electrode material particles bonded to said bottom of the pouch.

34. A bioelectrode as claimed in claim 26, wherein:
said electrode comprises particles of electrode material, a matrix for said electrode material particles, and an electric conductor covered by said matrix and in electric contact with said electrode material particles.

35. A bioelectrode as claimed in claim 26, wherein:
said electrode in said pouch extends into said electrolyte-absorbing means.

36. A bioelectrode as claimed in claim 26, wherein:
said electrolyte-absorbing means include an electrolyte-absorbing pad in physical contact with said electrode.

37. A bioelectrode as claimed in claim 26, wherein:
said electrolyte-absorbing means include a flexible electrolyte-absorbing pad spaced from said electrode and exposed at said aperture for contact with said body part, and an open-cell rigid member located between said flexible pad and said electrode for retaining electrolyte.

38. A bioelectrode as claimed in claim 26, wherein:
said bioelectrode includes and said pouch contains means for rigidifying said pouch.

39. A bioelectrode as claimed in claim 38, wherein:
said rigidifying means include an annulus encompassing at least said electrolyte-absorbing means.

40. A bioelectrode as claimed in claim 38, wherein:
said rigidifying means include a reinforcing member adjacent a portion of said pouch opposite said aperture.

41. A bioelectrode as claimed in claim 38, wherein:
said rigidifying means include a disk.

42. A bioelectrode as claimed in claim 26, wherein:
said electrode in said pouch includes a disk for supporting said electrolyte-absorbing means.

43. A bioelectrode as claimed in claim 26, wherein:
said electrolyte-absorbing means include an electrolyte-absorbing pad having a central bore exposed at said aperture for the reception of electrolyte.

44. A bioelectrode as claimed in claim 26, including:
a removable cover for said pouch; and
means for removably attaching said cover to said pouch to enclose said aperture.

45. A bioelectrode applicable to a body part, comprising in combination:
a pouch formed of electrically insulating material and having an aperture and a solid bottom remote from said aperture, and defining an enclosed interior wider than said aperture;
electric current conducting means including an electrode in said pouch spaced from said aperture and means for connecting said electrode to external electronic equipment;
electrolyte-absorbing means in said pouch in contact with said electrode and exposed at said aperture, said electrolyte-absorbing means extending in said enclosed interior beyond the width of said aperture; and
means in said pouch for rigidifying said pouch.

46. A bioelectrode as claimed in claim 45, wherein:
said rigidifying means include an annulus encompassing at least said electrolyte-absorbing means.

47. A bioelectrode as claimed in claim 45, wherein:
said rigidifying means include a reinforcing member adjacent a portion of said pouch opposite said aperture.

48. A bioelectrode as claimed in claim 45, wherein:
said rigidifying means include a disk.

49. A bioelectrode as claimed in claim 45, wherein:
said electrode in said pouch includes a disk for supporting said electrolyte-absorbing means.

50. A bioelectrode as claimed in claim 45, wherein:
said electrolyte-absorbing means include an electrolyte-absorbing pad having a central bore exposed at said aperture for the reception of electrolyte.

51. A bioelectrode as claimed in claim 45, including:
an adhesive sheet for facilitating application of said pouch to body parts, said pouch being located on said adhesive sheet with a portion of said adhesive sheet exposed in the direction of said electrolyte-absorbing means so that said electrolyte-absorbing means contact said body parts when said adhesive sheet retains said pouch on said body parts.

52. A bioelectrode as claimed in claim 45, including:
a removable cover for said pouch and means for removably attaching said cover to said pouch to enclose said aperture.

53. A bioelectrode as claimed in claim 45, wherein:
said electrode connecting means include an electric lead connected to said electrode and extending through said pouch to the outside of said pouch.

54. A bioelectrode as claimed in claim 45, wherein:
said pouch includes at least one sheet of electrically insulating watertight material, and a watertight seal interconnecting adjacent portions of said at least one sheet; and
said electrode connecting means include an electric lead connected to said electrode and extending through said watertight seal to the outside of said pouch.

55. A bioelectrode as claimed in claim 45, wherein:
said electrode is located on said bottom of the pouch.

56. A bioelectrode as claimed in claim 45, wherein:
said electrode is bonded to said bottom of the pouch.

57. A bioelectrode as claimed in claim 45, wherein:
said electrode comprises particles of electrode material and a matrix for said electrode material particles bonded to said bottom of the pouch.

58. A bioelectrode as claimed in claim 45, wherein:

said electrode comprises particles of electrode material, a matrix for said electrode material particles, and an electric conductor covered by said matrix and in electric contact with said electrode material particles.

59. A bioelectrode as claimed in claim 45, wherein: said electrode in said pouch extends into said electrolyte-absorbing means.

60. A bioelectrode as claimed in claim 45, wherein: said electrolyte-absorbing means include an electrolyte-absorbing pad exposed at said aperture for contact with said body part.

61. A bioelectrode as claimed in claim 60, wherein: said pad is in physical contact with said electrode.

62. A bioelectrode as claimed in claim 45, wherein: said electrolyte-absorbing means include a flexible electrolyte-absorbing pad spaced from said electrode and exposed at said aperture for contact with said body part, and an open-cell rigid member located between said flexible pad and said electrode for retaining electrolyte.

63. A bioelectrode applicable to a body part, comprising in combination:
a sheet of electrically insulating watertight material forming a pouch defining a closed interior and having a bottom formed by a portion of said sheet being solid throughout said bottom, and a top formed by a further portion of said sheet having an aperture remote from said bottom and being attached to said solid bottom-forming portion by a watertight seal integral with said solid bottom-forming portion and said further portion;
electric current conducting means including an electrode in said pouch spaced from said aperture and means for connecting said electrode to external electronic equipment; and
electrolyte-absorbing means in said pouch in contact with said electrode and exposed at said aperture.

64. A bioelectrode as claimed in claim 63, wherein: said sheet is folded upon itself to form said top and bottom; and
adjacent edge portions of said folded sheet are sealed to each other.

65. A bioelectrode as claimed in claim 63, wherein: said sheet is endless and has a solid portion forming said solid bottom and an apertured portion forming said top having said aperture; and
adjacent edge portions of said endless sheet are sealed to each other.

66. A bioelectrode as claimed in claim 63, wherein: said means for connecting said electrode to external electronic equipment include an electric lead connected to said electrode and extending in between said bottom formed by said solid portion of said sheet and said top formed by said further portion of said sheet through said seal to the outside of said pouch.

67. A bioelectrode applicable to a body part, comprising in combination:
a pouch having a bottom formed of a sheet of electrically insulating watertight material having a hole, and a top sealed to said bottom and having an aperture remote from said bottom, said pouch defining an enclosed interior wider than said aperture;
an electrode in said pouch spaced from said aperture;
means at said bottom for closing said hole with a watertight seal including an electric current conducting device connected to said electrode and extending through said hole to the outside of said pouch; and
electrolyte-absorbing means extending in said enclosed interior beyond the width of said aperture, being in contact with said electrode and accessible at said aperture.

68. A bioelectrode as claimed in claim 67, wherein: said means for closing said hole include an adhesive sheet for releasably retaining said pouch at said body part; and
said electric current conducting device has a portion extending through said adhesive sheet and said hole and means for clamping said adhesive sheet to said bottom at said hole.

69. A bioelectrode as claimed in claim 67, wherein: said electric current conducting device includes a snap fastener having two flanges clamping said bottom-forming sheet around said hole.

70. A bioelectrode as claimed in claim 67, wherein: said means for closing said hole include an adhesive sheet for releasably retaining said pouch at said body part; and
said electric current conducting device includes a snap fastener having a portion extending through said adhesive sheet and said hole and having two flanges clamping said adhesive sheet to said bottom at said hole.

71. A bioelectrode as claimed in claim 67, wherein: said bottom-forming sheet is flexible;
said bioelectrode includes a disk rigid relative to said bottom-forming sheet supporting said electrode in said pouch; and
said electric current conducting device extends through said disk at said hole.

72. A bioelectrode as claimed in claim 67, wherein: said bottom-forming sheet is flexible;
said bioelectrode includes a disk rigid relative to said bottom-forming sheet supporting said electrode in said pouch; and
said electric current conducting device has a portion extending through said disk and said hole and means for clamping said disk to said bottom at said hole.

* * * * *